(12) United States Patent
Rastegar

(10) Patent No.: US 10,571,378 B2
(45) Date of Patent: Feb. 25, 2020

(54) MECHANICAL ROTARY SHOCK TESTING MACHINES

(71) Applicant: Jahangir S Rastegar, Stony Brook, NY (US)

(72) Inventor: Jahangir S Rastegar, Stony Brook, NY (US)

(73) Assignee: OMNITEK PARTNERS LLC, Ronkonkoma, NY (US)

( * ) Notice: Subject to any disclaimer, the term of this patent is extended or adjusted under 35 U.S.C. 154(b) by 272 days.

(21) Appl. No.: 15/698,610

(22) Filed: Sep. 7, 2017

(65) Prior Publication Data

US 2018/0067030 A1    Mar. 8, 2018

Related U.S. Application Data

(63) Continuation of application No. 15/256,674, filed on Sep. 5, 2016, now Pat. No. 10,352,838.

(60) Provisional application No. 62/384,670, filed on Sep. 7, 2016.

(51) Int. Cl.
*G01N 3/31* (2006.01)
*G01N 3/307* (2006.01)
*F42B 35/00* (2006.01)
*F42B 30/02* (2006.01)

(52) U.S. Cl.
CPC .......... *G01N 3/307* (2013.01); *F42B 30/02* (2013.01); *F42B 35/00* (2013.01); *G01N 3/31* (2013.01); *G01N 2203/0035* (2013.01); *G01N 2203/0042* (2013.01); *G01N 2203/0204* (2013.01); *G01N 2203/0647* (2013.01)

(58) Field of Classification Search
None
See application file for complete search history.

(56) References Cited

U.S. PATENT DOCUMENTS

| | | | | |
|---|---|---|---|---|
| 2,799,824 A * | 7/1957 | Heynick | ............... | H01J 9/42 |
| | | | | 324/413 |
| 2,846,869 A * | 8/1958 | Tyler | ............... | G01P 21/00 |
| | | | | 73/12.06 |
| 6,308,555 B1 * | 10/2001 | Liem | ............... | G01N 3/303 |
| | | | | 73/12.01 |
| 6,871,833 B1 * | 3/2005 | Zeh | ............... | F15B 21/12 |
| | | | | 251/129.2 |
| 9,970,844 B2 * | 5/2018 | Rastegar | ............... | G01M 7/08 |
| 10,190,937 B2 * | 1/2019 | Rastegar | ............... | G01M 7/08 |
| 10,352,838 B2 * | 7/2019 | Rastegar | ............... | G01N 3/31 |
| 2005/0104697 A1 * | 5/2005 | Fletcher | ............... | G01M 7/04 |
| | | | | 335/220 |
| 2006/0272390 A1 * | 12/2006 | Grossman | ............... | G01N 3/62 |
| | | | | 73/12.09 |

(Continued)

*Primary Examiner* — Andre J Allen

(57) ABSTRACT

A rotary shock-testing machine including: a base; a first shaft rotatable relative to the base, the first shaft being driven to rotate; a first wheel rotatable with the first shaft; a second shaft rotatable relative to the base; a second wheel rotatable with a first portion of the second shaft; and a test disc for holding one or more specimens to be tested, the test disc being rotatable with a second portion of the second shaft; wherein the first and second wheels are aligned with each other such that the second wheel is driven by the first wheel when a material is introduced into a gap between a surface of the first wheel and a corresponding surface of the second wheel.

7 Claims, 11 Drawing Sheets

(56) References Cited

U.S. PATENT DOCUMENTS

2006/0272423 A1\* 12/2006 Grossman ............... G01N 3/31
                                                                                  73/779

\* cited by examiner

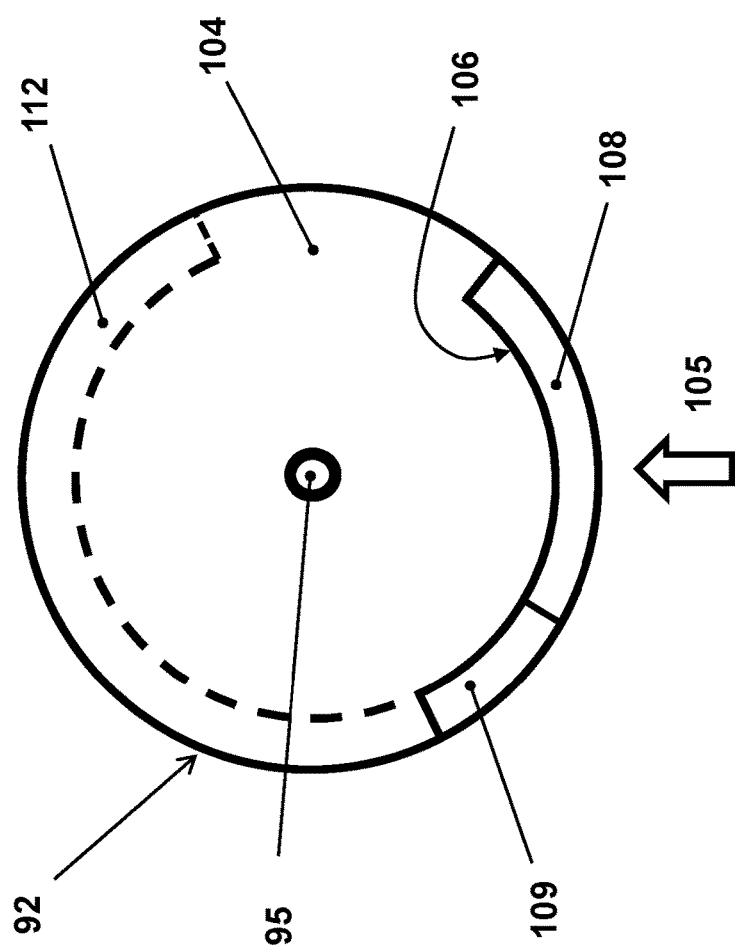
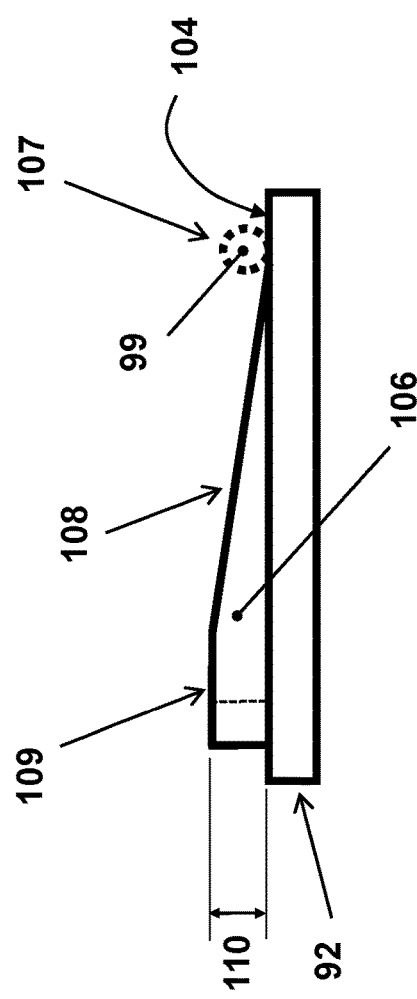

MECHANICAL ROTARY SHOCK TESTING MACHINES

CROSS REFERENCE TO RELATED APPLICATION

This application is a continuation-in-part of U.S. patent application Ser. No. 15/256,674 filed on Sep. 5, 2016, and claims the benefit to U.S. Provisional Application No. 62/384,670 filed on Sep. 7, 2016, the entire contents of each of which are incorporated herein by reference.

BACKGROUND OF THE INVENTION

1. Field of the Invention

The present invention relates generally to a spin-shock testing machine for subjecting the components to be tested to a rotary acceleration pulse of a prescribed amplitude and duration, and more particularly for testing various devices and components of rifled gun-fired munitions as well said munitions by subjecting them to similar launch spin acceleration pulses generated by the gun barrel rifling.

2. Prior Art

Munitions fired from guns with rifled barrels are subjected to high rotary acceleration pulse as they are accelerated in rotation to their muzzle exit spin rates, generally to achieve highly stabilized flight. Spin deceleration is also encountered as munitions impact the target. As a result, all components of the munitions and the assembled munitions itself must survive the said shock loading event due to the imparted high rotary acceleration pulse and be qualified to such severe environments.

Component testing for survivability during the firing and for operational performance and qualification testing, particularly during the development phase, cannot usually be done in an actual environment on complete assemblies. In addition to prohibitive cost involved, testing of components in actual environments would not provide the required information for evaluating the component design and performance and for optimizing its design parameters. In addition, in many cases the performance of a component can only be determined while integrated in a system or sub-system. For these reasons, laboratory simulations of the shock loading environments are highly desirable for testing individual components, sub-assemblies and sometimes the complete system assembly.

Gun-fired munitions, mortars and rail-gun munitions are also subjected to high-G linear (setback and set-forward) acceleration during the launch and upon target impact. In some applications, lateral acceleration shock is also considerable. As a result, all components of the system and the system itself must survive the said shock loading events and be qualified to such severe environments. For this reason, shock-loading machines that to varying degrees simulate firing setback acceleration environments have been developed.

In the current state of the art, firing setback (linear) acceleration based shock loading environments are simulated in the industry by one of the following methods:

1. Electro-Dynamic Shaker.
    This method can accurately produce a desired shock response spectrum (SRS) within closely specified tolerances, but amplitude and frequency limitations of the equipment greatly restrict its applicability.

2. Live Ordnance with System Structure.
    Since the actual system structure and live ordnance are used, this method has the potential to produce a shock virtually identical to the expected field environment. The cost of the test structure, however, is usually prohibitive. The use of live ordnance may have a wide repeatability tolerance, and does not easily allow the test levels to be increased so that an adequate design margin can be assured. For the case of gun-fired munitions, mortars and the like, the added problem is the "soft" recovery of the launched round to examine the state of the components being tested. In certain case, telemetry of data may be used to transmit back data related to the operation of certain components. However, in most cases it is highly desirable to examine the state of the components post firing. In addition, in many cases it is extremely difficult if not impossible to measure/determine the effect of shock loading on many components for transmission to a ground station via telemetry. Visual observation of the dynamic behavior of the various mechanical elements and mechanisms and other components, such as electrical and electronic and sensory elements, and their interaction with the munitions structure, is almost nearly impossible in most cases. Such visual observations are highly desirable for determining their dynamic behavior under shock loading, for identifying their modes of failure, and ultimately for the purpose of arriving at their optimal designs.

3. Live Ordnance with Mock Structure.
    This method has most of the same features as the method "2" above, except that some cost savings are attributed to the use of a mass mock-up structure. These savings may be negated by the need for some trial-and-error testing to attain the desired component input, where geometric similarity was used in method "2" above to attain the same result. This method also suffers from the same shortcomings for testing components of gun-fired munitions and mortars and the like as indicated for the above method "2".

4. Live Ordnance with Resonant Fixture.
    This method further reduces test cost, and is a candidate for general purpose testing, due to the use of a generic resonant plate fixture. Since live ordnance is used, all the very high frequencies associated with near-field pyrotechnic shock events are produced with this method. However, a great amount of trial-and-error testing may be required to obtain the desired component input. This method also suffers from the same shortcomings for testing components of gun-fired munitions as indicated for the above method "2" and amplitude and duration of the above method "1".

5. Mechanical Impact with Mock Structure.
    Mechanical impacts do not produce the very high frequencies associated with the stress pulse in the immediate vicinity of a pyrotechnic device. However, most components in a typical system are isolated by enough intermediary structure such that the shock at the component location is not dominated by these very high frequencies. Instead, the shock at the component is dominated by the structural response to the pyrotechnic device, and has dominant frequencies which are typically less than 10 KHz. For these components, a mechanical impact (e.g. using a projectile or pendulum hammer) can produce a good simulation of the pyrotechnic shock environment. Test amplitudes can easily be increased or decreased by simply increasing or decreasing the impact speed. The shock level and duration can be controlled to some extent by the use of various pads affixed at the point of impact. According to this method, attempt is made to subject the structure containing the test components the impact induced acceleration (shock) profile, which close to that experienced when assembled in the actual system. The test conditions are experimentally adjusted to achieve an approximation of the actual acceleration (shock) profile. In general, a large amount of trial-and-error runs have to be made to achieve an acceptable acceleration (shock) profile. The characteristics and response of the various pads used at the impact point to increase the duration of the shock (acceleration) event is generally highly variable and dependent on temperature and moisture. In addition, due to inherent design of such mechanical impact machines and the limitations on the thickness of the pads that can be used at the impact point, high G acceleration peaks with long enough duration similar to those, e.g., experienced by munitions fired large caliber guns or mortars, cannot be achieved. For example, to achieve a peak shock acceleration level of 5000 G with a duration of 4 milliseconds, the said pad deformation has to be well over 0.6 meters (considering a reasonable ramp-up and ramp-down of 0.1 meters each), which is highly impractical. It is also appreciated by those skilled in the art that for simulating firing (setback) acceleration for most gun-fired munitions and mortars, the peak acceleration levels can generally be well over the considered 5000 Gs with significantly longer durations. It can therefore be concluded that the described mechanical impact machines do not accurately duplicate the shock profile experienced by munitions during firing or target impact and are not suitable for accurate shock testing of components to be used in such munitions.

6. Mechanical Impact with Resonant Fixture.

In this method, a resonant fixture (typically a flat plate) is used instead of a mock structure. This significantly reduces cost, and allows for general purpose testing since the fixturing is not associated with a particular structural system. The mechanical impact excites the fixture into resonance which provides the desired input to a test component mounted on the fixture. Historically, test parameters such as plate geometry, component location, impact location and impact speed have been determined in a trial-and-error fashion. In general, this method produces a simulated environment which has its energy concentrated in a relatively narrow frequency bandwidth. It should be noted here that a suitable resonant fixture for use in this method may also be a bar impacted either at the end or at some point along the length of the bar. This method is suitable for many applications in which the components are subjected to relatively long term vibration such as those induced by the system structure. The method is, however, not suitable for testing components of gun-fired munitions and the like since in such cases the munitions is subjected primarily to a single very high G setback or impact shock with relatively long duration.

7. Air-Gun Testing Platforms.

In this method, the components to be tested are usually mounted in a "piston" like housing with appropriate geometry. In one method, the said "piston" is then accelerated by the sudden release of pressurized air or accelerated by the rupture of a diaphragm behind which air pressure is continuously increased until the diaphragm is failed in sheared. In another type of air gun a similar air tight "piston" within which the components to be tested are securely mounted is accelerated over a certain length of a tube by pressurized gasses. The "piston" is thereby accelerated at relatively slower rates and once it has gained a prescribed velocity, the "piston" existing the tube and impacts decelerating pads of proper characteristics such as aluminum honeycomb structures to achieve the desired deceleration amplitude and duration. The components are assembled inside the "piston" such that the said deceleration profile to correspond to the desired actual shock (acceleration) profile. In general, similar to the above method "5", air guns can be used to subject the test components to high G shock (acceleration) levels of over 30,000 Gs but for durations that are significantly lower than those experienced by gun-fired munitions, mortars and the like. It can therefore be concluded that the described mechanical impact machines do not accurately duplicate the shock profile experienced by munitions during firing or target impact and are not suitable for accurate shock testing of components to be used in such munitions. Air guns in which the said test component carrying piston is subjected to the acceleration pulse by the sudden release of pressurized air or is accelerated by the rupture of a diaphragm, the air gun may also be provided with sections that applies rotary acceleration (spin acceleration) to the piston. However, similar to the indicated case of linear acceleration pulses, the pulse durations that can be generated are significantly shorter than those experienced by gun-fired munitions and the like. It can therefore be concluded that the (spin) rotary acceleration pulses that can be generated by current air guns do not accurately duplicate the rotary shock profile experienced by munitions during firing or target impact and are not suitable for accurate rotary shock testing of components to be used in such munitions.

8. Rocket Sleds.

Rocket sled is a test platform that slides along a set of rails, propelled by rockets. As its name implies, a rocket sled does not use wheels. Instead, it has sliding pads, called "slippers", which are curved around the head of the rails to prevent the sled from flying off the track. The rail cross-section profile is usually that of a Vignoles rail, commonly used for railroads. Rocket sleds are used extensively in aerospace applications to accelerate equipment considered too experimental (hazardous) for testing directly in piloted aircraft. The equipment to be tested under high acceleration or high airspeed conditions are installed along with appropriate instrumentation, data recording and telemetry equipment on the sled. The sled is then accelerated according to the experiment's design requirements for data collection along a length of isolated, precisely level and straight test track. This system is not suitable for testing components for gun-fired munitions and mortars and the like since it can produce only around 100-200 Gs.

9. Soft Recovery System Facility (SCat Gun)

In this system, the components to be tested are packaged inside a round, which is fired by an actual gun (in the current system located at the U.S. Army Armament Research, Development and Engineering Center (ARDEC) in New Jersey, with a 155 mm round being fired by a 155 mm Howitzer weapon with a M199 gun tube and 540 feet of catch tubes). The projectile is then recovered using a "Soft Recovery" system. The soft catch component of the system uses both pressurized air and water to help slow down the projectile. The first part of the chain of catch tubes only contains atmospheric air. The next section, 320 feet of the tubes, contains pressurized air, followed by an 80 feet section that is filled with water. A small burst diaphragm seals one end of the pressurized air and a piston seals the other end. The piston also separates the water and pressurized air sections. The burst diaphragm and piston are replaced after each test fire. Once fired, the projectile achieves free flight for approximately 6 feet and travels down the catch tubes, generating shockwaves that interact with the atmospheric air section, the burst diaphragm, the pressurized air section, the piston and the water section. The air section is compressed and pushed forward and shock and pressure cause the piston move against the water, all while slowing the projectile to a stop. Then the piston is ejected out of the end of the system, followed by the air and water, and finally the projectile comes to rest in a mechanized brake system. On-board-recorders inside the projectile measure the accelerations of the projectile from the gun-launch and the catch events. This system currently provides the means to subject the test components to as realistic firing shock loading conditions, including the rotary (spin) acceleration shock loading pulse, as possible and provides the means to retrieve the round to examine the tested components. The cost of each testing is, however, very high, thereby making it impractical for use for engineering development. The system is also impractical for use for most reliability testing in which hundreds and sometimes thousands of samples have to be tested and individually instrumented. It also takes hours to perform each test.

The methods 1-6 described above are more fully explained in the following references: Daniel R. Raichel, "Current Methods of Simulating Pyrotechnic Shock", Pasadena, Calif.: Jet Propulsion Laboratory, California Institute of Technology, Jul. 29, 1991; Monty Bai, and Wesley Thatcher, "High G Pyrotechnic Shock Simulation Using Metal-to-Metal Impact", The Shock and Vibration Bulletin, Bulletin 49, Part 1, Washington D.C.: The Shock and Vibration Information Center, September, 1979; Neil T. Davie, "The Controlled Response of Resonating Fixtures Used to Simulate Pyroshock Environments", The Shock and Vibration Bulletin, Bulletin 56, Part 3, Washington D.C.: The Shock and Vibration Information Center, Naval Research Laboratory, August 1986; Neil T. Davie, "Pyrotechnic Shock Simulation Using the Controlled Response of a Resonating Bar Fixture", Proceedings of the Institute of Environmental Sciences 31st Annual Technical Meeting, 1985; "The Shock and Vibration Handbook", Second Edition, page 1-14, Edited by C. M. Harris and C. E. Crede, New York: McGraw-Hill Book Co., 1976; Henry N. Luhrs, "Pyroshock Testing—Past and Future", Proceedings of the Institute of Environmental Sciences 27th Annual Technical Meeting, 1981.

The aforementioned currently available methods and systems mostly for testing components to be used in various systems that subject them to linear acceleration (shock) events, except for the method and system "7" (air-gun testing platform) and "9" (Soft Recovery System Facility—SCat Gun), that can apply high rotary (spin) acceleration shock loading pulse to the components being tested. The methods and systems "7" and "9", however, suffer from a number of indicated shortcomings that make them unsuitable for testing components and systems during engineering development and evaluation process for spinning gun-fired munitions and the like.

For the case of method and system "7" (air-gun testing platforms), similar to the applied linear (setback) acceleration pulses, the duration of the rotary acceleration pulses are significantly shorter than those experienced by gun-fired munitions and the like. It can therefore be concluded that the (spin) rotary acceleration pulses that can be generated by current air guns do not accurately duplicate the rotary shock profile experienced by munitions during firing or target impact and are not suitable for accurate rotary shock testing of components to be used in such munitions.

For the case of method and system "9" (Soft Recovery System Facility—SCat Gun), the cost of each testing is very high, thereby making it impractical for use for engineering development. The system is also impractical for use for most reliability testing in which hundreds and sometimes thousands of samples have to be tested and individually instrumented. It also takes hours to perform each test.

In addition to the above shortcomings, the method and system "7" (air-gun testing platform) and "9" (Soft Recovery System Facility—SCat Gun) cannot provide the means of visually observing (e.g., video recording) the dynamic behavior of the various mechanical elements and mechanisms and other components, such as electrical and electronic and sensory elements, and their interaction with the munitions structure. Such visual observations are highly desirable for determining their dynamic behavior under shock loading, for identifying their modes of failure, and ultimately for the purpose of arriving at their optimal designs.

SUMMARY OF THE INVENTION

A need therefore exists for the development of novel methods and resulting testing apparatus (rotary shock testing machines) for testing components of spin stabilized gun-fired munitions and other devices and systems that are subjected to high and long duration rotary acceleration pulsed (shock loading) during firing by rifled barrels. Such rotary acceleration pulses that are experienced by gun-fired munitions, particularly larger caliber munitions, may have durations of up to 10-15 milliseconds and may be used to accelerate the round to spin rates in excess of 200-300 Hz.

A need also exists for methods that are not be based on the use of the actual or similar platforms, for example, firing projectiles carrying the test components with similar guns such as the described in the method "9" above, due to the cost and difficulty in providing full instrumentation which would allow testing of a few components at a time, thereby making the cost of engineering development of such components and their reliability testing which requires testing of a large number of samples prohibitively high.

A need also exists for novel mechanical rotary shock testing machines that can provide the means of testing a large number of fully instrumented components in a relatively short time. This requires that the said mechanical shock testing machine allows rapid mounting of test components onto the test platform while allowing relatively free access to the said components, unlike the "piston" platforms used in air guns (aforementioned method "7") or inside projectiles that are gun-launched (aforementioned method "9").

The novel mechanical rotary sock testing must also provide highly predictable and repeatable rotary shock loading (acceleration) profile for testing the intended components so that the results can be used for detailed analytical model validation and tuning; for predicting the performance of the components in actual applications; and for providing the required information for the design of the said components and optimization of the developed designs.

Herein is described a novel method for the design of rotary shock testing machines and the resulting rotary shock testing machines that can subject test components and systems to high rotary acceleration pulse (shock) of relatively long duration. The resulting rotary shock testing machines are shown to address the aforementioned needs and are particularly suitable for engineering development and testing of components to be used in spin stabilized munitions fired from guns with rifled barrels.

In addition, a need also exists for the development of novel methods and resulting testing apparatus (rotary shock testing machines) for testing components of spin stabilized gun-fired munitions and other devices and systems that are subjected to high and long duration rotary acceleration pulsed (shock loading) during firing by rifled barrels from their stationary state in the gun breach to their gun barrel spin rate. Such rotary acceleration pulses from their stationary state in the gun breach to their gun barrel exit spin rate that are experienced by gun-fired munitions, particularly larger caliber munitions, may have durations of up to 10-15 milliseconds and may be used to accelerate the round to spin rates in excess of 100 Hz.

In addition, since during firing of munitions in rifled barrels, the munitions is subjected to linear acceleration in the direction of its travel inside the barrel as well as the aforementioned spin acceleration about the direction of its travel, therefore it is also highly desirable to provide methods of designing and constructing shock loading machines that can impart a combination of linear acceleration shock loading as well as spin acceleration shock loading to the munitions systems and/or its components to be tested.

It will be appreciated by those having ordinary skill in the art that in munitions firing in rifled barrels, the spin acceleration rate and the linear acceleration rates are related and are not independent and the relationship is dependent on the pitch of the rifling inside the barrel. It will also be appreciated by those having ordinary skill in the art that in certain applications, spin acceleration may be provided to the munitions being fired inside or outside the barrel by means other than rifling. The spin acceleration shock loading machines provided herein can also be used to simulate such shock loading events for testing munitions systems and their components.

A need also exists for the development of methods and resulting testing apparatus for testing components of spin stabilized gun-fired munitions and other devices and systems in a combination of high rotary and linear acceleration shock loading similar to those experienced during firing by rifled barrels.

Also provided herein are methods for the design of rotary shock testing machines and the resulting rotary shock testing machines that can subject test components and systems to high rotary acceleration pulse (shock) of relatively long duration from their stationary state to their final spin rate. Also provided are shock-testing machines that can subject test components and systems to a combination of high rotary and linear acceleration shock loading similar to those experienced during firing by rifled barrels. The resulting shock testing machines are shown to address the aforementioned needs and are particularly suitable for engineering development and testing of components to be used in spin stabilized munitions fired from guns with rifled barrels.

BRIEF DESCRIPTION OF THE DRAWINGS

These and other features, aspects, and advantages of the apparatus of the present invention will become better understood with regard to the following description, appended claims, and accompanying drawings where:

FIG. 11 illustrates a view of a back surface of the testing platform disc of the shock-loading embodiment of FIG. 10 showing a design and operation of the linearly accelerating cam of this machine.

FIG. 12 illustrates a side view of the testing platform disc of the shock-loading embodiment of FIG. 10 as seen in the direction of the arrow shown in FIG. 11.

DETAILED DESCRIPTION OF THE PREFERRED EMBODIMENT

Figure 1:
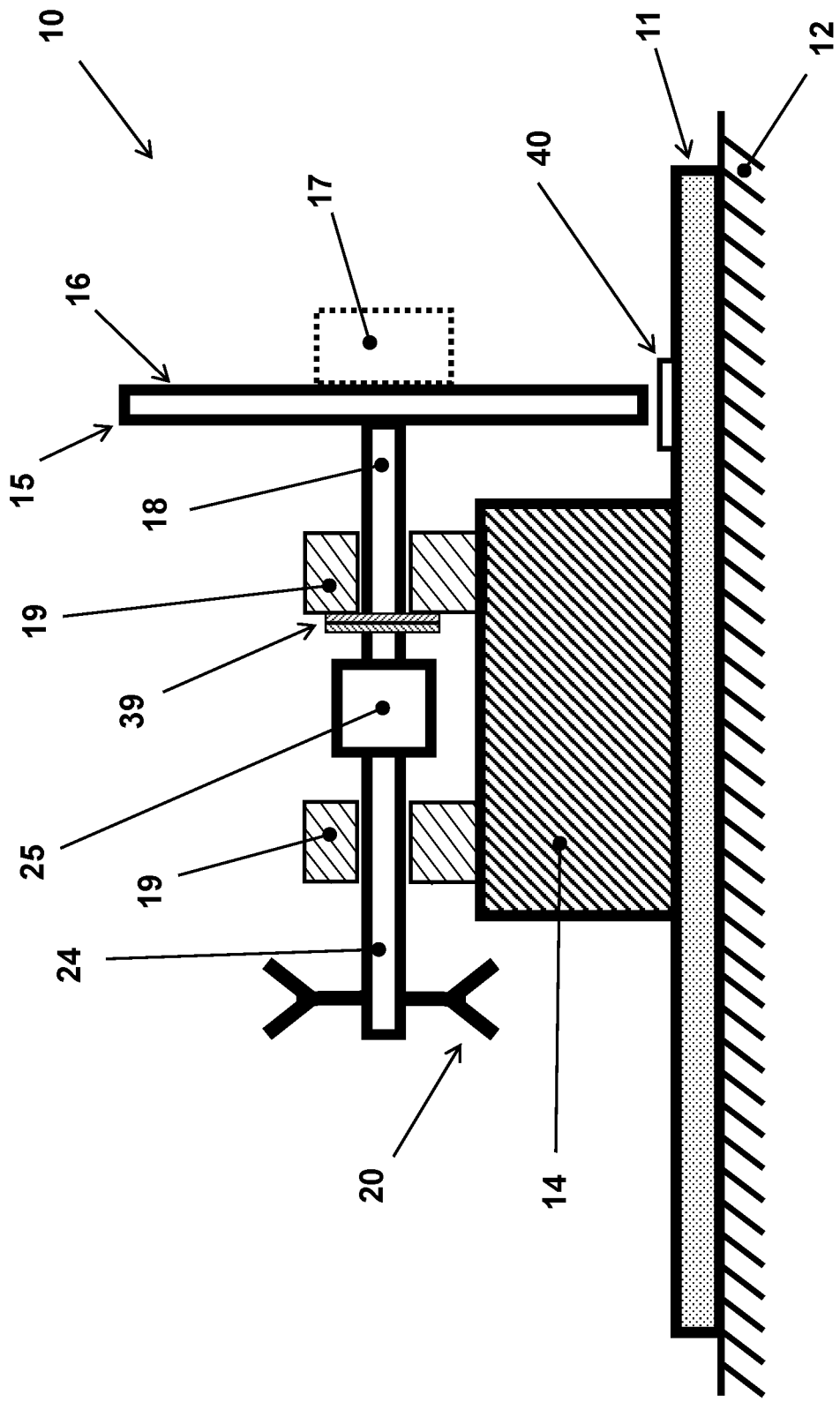
FIG. 1 illustrates the schematic of a cross-sectional side view of the basic embodiment of the mechanical rotary shock-testing machine.
Figure 2:
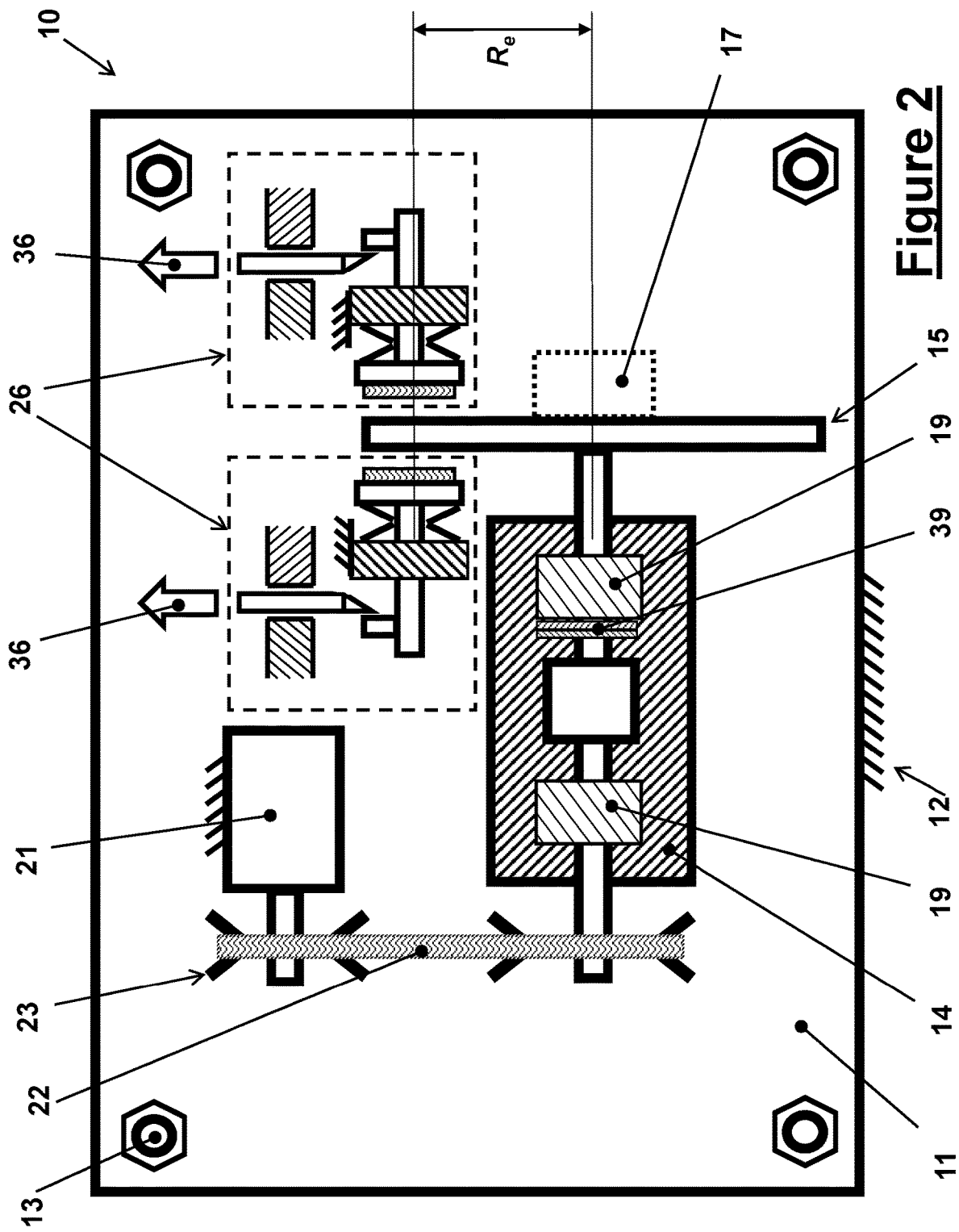
FIG. 2 illustrates the top view of the basic mechanical rotary shock testing machine embodiment of FIG. 1.

The basic design and operation of the mechanical rotary shock-testing machine is shown in the schematic of FIG. 1 and is indicated as the embodiment 10. The mechanical rotary shock testing machine 10 is constructed over a base plate 11, which can be made out of a heavy and thick steel plate which is firmly anchored to the machine foundation 12 by at least four heavy anchoring bolts (13 in FIG. 2) that are far enough apart around the base plate to resist the high torque reaction pulses (shocks) in reaction to the rotary shock loading pulses generated by the mechanical rotary shock testing machine 10. The top view of this embodiment 10 of the mechanical rotary shock-testing machine is shown in FIG. 2. Certain relatively stiff shock absorbing elements (not shown) may be provided between the base 11 and the foundation 12 to prevent damage to the foundation structure. In heavier machinery, a relatively large (usually made out of reinforced concrete) foundation block (not shown) can be used with shock isolation elements having been positioned between the foundation block and the surrounding structure.

In the embodiment 10 shown in the cross-sectional and top views of FIGS. 1 and 2, respectively, a rigid platform structure 14 is firmly attached to the base plate 11 and is used to rigidly attach the rotary assembly of the mechanical rotary shock-testing machine to the base plate 11 as described below.

The mechanical rotary shock testing machine 10 is provided with a "testing platform" disc 15, over the frontal surface of which 16 the components to be tested 17 are generally attached. The testing platform disc 15 is rigidly attached to a shaft 18, FIG. 1, which is supported by one or more bearings 19. The shaft 18 is provided with a pulley 20, which is used to rotate the shaft 18 by an electric motor 21 via a belt 22 and the motor pulley 23, FIG. 2. The electric motor 21 is firmly attached to the base plate 11. The speed of the electric motor 21 can be controlled by a computer (not shown) as is commonly done in various machinery. The shaft 18 can be made out of two sections, the aft section of which is connected to the front portion to which the testing platform disc 15 is attached by a coupling 25 as shown in FIG. 1. The coupling can also be a one-way clutch or can be provided with a one-way clutch so that as the disc 15 is subjected to a deceleration pulse through the engagement of the provided braking mechanisms as described later in this disclosure, the aft section 24 of the shaft 18 and thereby the electric motor and the motion transmitting pulley and belt system are disengaged from the testing platform disc 15. In practice, multiple bearing units 19 can be used on each section of the shaft 18 to minimize its deflection and to allow it to be rotated at the highest operating speed that the machine is designed to operate.

Figure 3:
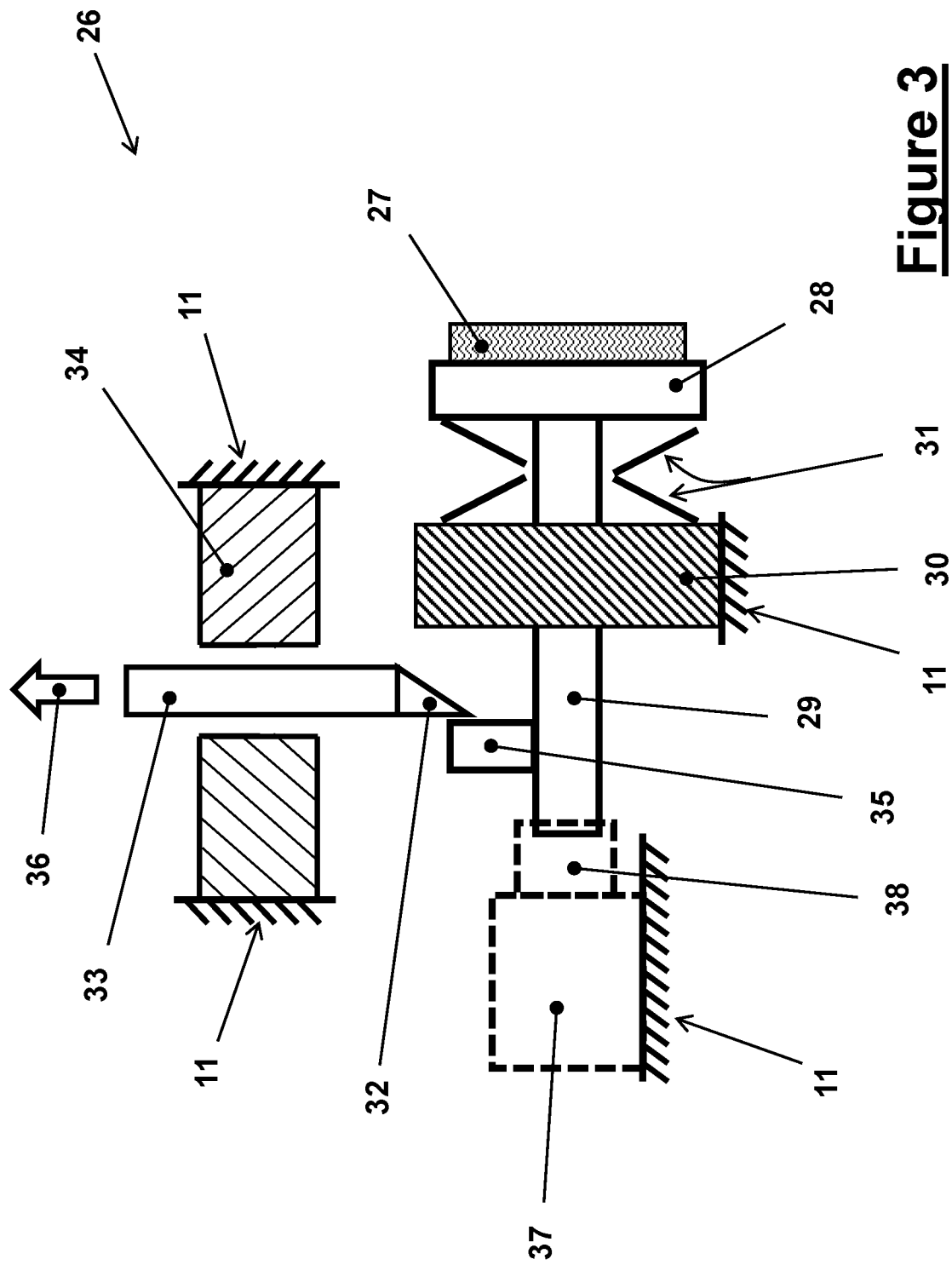
FIG. 3 illustrates the schematic of the braking units of the basic embodiment of the mechanical rotary shock-loading machine of the present invention shown in the schematics of FIGS. 1 and 2.

The testing platform disc 15 is provided with at least one braking units 26, FIG. 2, the details of which is shown in the schematic of FIG. 3. The braking units 26 are designed to engage the testing platform disc 15 very rapidly upon command and apply a nearly constant braking force and thereby a nearly constant decelerating torque to the testing platform disc 15 as it rotates at certain speed as described in detail below.

The braking unit 26, a schematic of which is shown in FIG. 3, can consist of a braking pad 27, which is fixedly attached to a rigid backing plate 28. The backing plate 28 is fixedly attached to the sliding member 29, which can slide back and forth (to the right and to the left as seen in the schematic of FIG. 3) in the linear bearing 30, which is fixedly attached to the base plate 11. The linear bearing 30 may be constructed to be free to rotate about its longitudinal axis or may be provided with guides or shaped (for example with a square cross-section) to prevent it from rotating. In one embodiment, a compressive spring 31, which can consist of a set of Belleville washers, is provided between the backing plate 28 and the linear bearing. Before performing a rotary shock-loading test, the compressive spring 31 is preloaded in compression to a prescribed level and held in the preloaded position by the tip 32 of the sliding locking member 33, which engages the provided member 35 on the sliding member 29. The sliding locking member 33 is constructed to slide up and down, as seen in the schematic of FIG. 3, inside the guiding bearing 34. The sliding locking member 33 can be biased downward in the engaged position with the member 35 of the sliding member 29 by a spring (not shown).

The level of the aforementioned prescribed compressive preloading of the compressive spring 31 is selected such that considering the gap between the braking pad 27 and the engaging surfaces of the testing platform disc 15, FIG. 2, once sliding member 29 is released by the pulling of the sliding locking member 33 in the direction of the arrow 36, the force with which the braking pad 27 presses against the surface of the testing platform disc 15 generates a desired level of friction force while the disc 15 is rotating. It is appreciated that while the testing platform disc 15 is rotating, the friction forces generated by the at least one braking pad 27 would apply a rotationally decelerating torque to the testing platform disc 15. In practice, depending on the combined moment of inertia about the axis of rotation of the testing platform disc 15, the payload 17, the shaft 18 and the inertia contributed by the coupling 25, and the desired rotary deceleration rate at which the payload is desired to be tested, the required level of the braking pad generated torque is determined.

The level of preloading of the compressive spring 31 may be adjusted in many different ways. One simple method consists of placing shim plates of appropriate thickness between the compressive spring 31 and the linear bearing 30. When the level of compressive preloading required is very high, a hydraulic cylinder 37 with the piston 38 shown in FIG. 3 and fixed to the base plate 11 may be used to pull on the sliding member 29 until the tip 32 of the sliding locking member 33 can engage the member 35 and maintain the compressive spring 31 at the desired preloading level.

In an alternative embodiment, the braking unit 26 can be provided with a hydraulic or pneumatic cylinder 37, which is shown in FIG. 3 by dashed lines. The piston 38 of the hydraulic (pneumatic) cylinder is then attached to the sliding member 29 and is used to drive the braking pad 27 to engage the surface of the testing platform disc 15 and apply the desired level of force corresponding to the aforementioned decelerating toque pulse. The hydraulic (pneumatic) pressure of the cylinder 37 is readily provided by commonly used hydraulic (pneumatic) sources (not shown) with manual or automatic pressure adjustment capability which are well known in the art. In general, pneumatic systems are preferable over hydraulic systems since they are less costly, easier to operate, cleaner and require less maintenance. However, hydraulic pistons can be pressurized to significantly higher pressures, thereby occupying less space.

One advantage of using hydraulically or pneumatically operating braking units is that they provide the means of rapidly varying the decelerating torque level that is applied to the testing platform disc 15. However, in general, braking unit 26 that operates with the preloaded springs 31, particularly when relatively small Belleville washers are used for this purpose, can engage the testing platform disc 15 and apply the peak decelerating toque significantly faster than is possible with pneumatic and even hydraulic systems due to the significantly lower inertia of its moving parts, noting that in pneumatic and hydraulic systems the inertia of the piston as well as displaced air and hydraulic fluid must also be considered.

To perform a rotary shock testing of certain components 17, the components are firmly mounted on the surface 16 of the testing platform disc 15 as shown in FIGS. 1 and 2. The testing platform disc 15 can be provided with patterns of threaded and pin holes for mounting the components directly or via appropriate fixtures to the surface 16 of the testing platform disc 15. The testing platform disc 15 with the mounted components 17 is then balanced. For relatively low spin rates, gravity based balancing (also referred to as static balancing in the art for vehicular wheel balancing) is usually enough. This can be done by slowly rotating the disc in the direction of one-way clutch 25 disengagement, and stopping every around 10-15 degrees to see if the otherwise stationary wheel would begin to continue to rotate due to an imbalance mass. If so, the operator will keep rotating the wheel a few degrees at a time until the disc would not rotate any further. This process would position the equivalent imbalance mass at its lowest elevation. The process is made easier if the operator can quickly disengage the one-way clutch 25, in which case the equivalent imbalance mass will automatically settle to its lowest elevation position. The one-way clutch 25 may, for example, be designed for quick disengagement by attaching it to the shaft 18 by a readily removable pin or key (not shown). A counterweight of proper mass can then be fixedly attached to the testing platform disc 15 at one or two symmetrically positioned threaded or through holes provided on the opposite side of the equivalent imbalance mass position to balance the testing platform disc 15 assembly with the attached testing component 17.

It will be appreciated by those skilled in the art that the method of balancing the testing platform disc 15 assembly with the attached testing component 17 is very similar to that of balancing vehicular wheels. As such, when the rotary speed (spin rate) at which the deceleration shock loading pulse is intended to be applied is high, the testing platform disc 15 assembly with the attached testing component 17 may be required to be balanced dynamically, such as following an aforementioned gravity (static) balancing, as it is commonly done for vehicular wheels.

Once the testing platform disc 15 assembly with the attached testing component 17 is balanced, the one-way clutch 25 is re-engaged and the testing platform disc 15 is accelerated very slowly to the rotary speed (spin rate) at which the prescribed deceleration shock loading pulse is to be applied to the component 17 that is being tested.

Once the testing platform disc 15 has reached its required rotary speed, the sliding locking member 33 is pulled in the direction of the arrow 36, FIGS. 2 and 3, thereby releasing the sliding member 29 and causing the at least one braking pad 27 to engage the surface of the testing platform disc 15 with the prescribed force generated by the preloaded spring 31. The friction forces generated by the braking pads 27 in turn generate the required torque to the rotating testing platform disc 15 to decelerate it at the desired rate.

When hydraulic or pneumatic cylinder 37 is used instead of the preloaded spring 31, the sliding member 29 is displaced by the piston 38 of the cylinder 37 towards the rotating testing platform disc 15. The braking pad 27 will then similarly engage the surface of the testing platform disc 15 and the torque required to decelerate the testing platform disc 15 at the desired rate is thereby generated.

As it is indicated above and appreciated by those skilled in the art, the reason for using braking unit 26 that operate with preloaded Belleville washer type springs 31 is so that full braking torque can be applied to the testing platform disc 15 very rapidly so that rotary shock loading pulse experienced during munitions firing can be nearly duplicated for testing various components used in munitions. It is appreciated that during firing of munitions in rifled barrels the rotary shock loading pulsed is applied to the round within as little as 1-2 milliseconds, which is not possible to achieve by hydraulically or pneumatically actuated braking mechanisms. In cases where significantly slower application of the braking torque is acceptable, then floating caliper type disc brakes similar to those commonly used in vehicles can be used. Such disc braking systems are well known in the art.

In general, the motor 21 is computer controlled and is provided with a position and possibly a rotational velocity sensor to allow the application of the desired acceleration and velocity profile to bring the testing platform disc 15 to the desired spin rate before the application of the deceleration pulse as previously described. It is, however, also possible to have the capability to continuously measure the position, velocity and acceleration of the testing platform disc 15 directly. Such measurements are direct measurements of the state of the testing platform disc and the component being tested 17, but more importantly, they can be used to directly measure the deceleration pulse profile that is applied to the component that is being tested 17. As a result, the component itself does not have to be instrumented by inertia sensors such as accelerometers to measure the profile of the deceleration profile. Such a sensor 40, FIG. 1, for measuring the position, velocity and acceleration of the testing platform disc 15 can be non-contact, such as optical sensors reading finely spaced lines on the edge or side of the disc, similar to commonly used optical encoders or bar code readers. It will be appreciated to those skilled in the art that in such optical sensors, for example when detecting the edge of equally spaced lines drawn or otherwise formed on the side of the testing platform disc 17 (parallel to the direction of axis of rotation of the disc), by increasing the number of lines over the disc periphery, and/or by using multiple rows of lines that are differently spaced, and/or by using multiple detectors that are properly spaced, as well as by using the time and velocity information between each detected lines, the resolution of the position, velocity and deceleration pulse profile measurements can be significantly increased. Such optical sensors and their operation and methods of increasing their measurement precision are well known in the art.

Alternatively, instead of an optical sensor, the sensor 40 may be a gap measuring sensor with the side surface of the testing platform disc 15 having been provided with linear or the like shallow grooves. Then as each groove passes the sensor the sensor electronic would count the number of such passing and thereby together with time information can determine the position, velocity and acceleration profile of the disc as a function of time. Such sensory systems and their computational algorithms for measuring linear and rotary position, velocity and acceleration in various machinery are well known in the art.

It will be appreciated by those skilled in the art that by using one of the above non-contact sensors 40 for measuring the rotational position, velocity and acceleration of the testing platform disc 15 as a function of time, then the need for a more complex system of slip rings for powering instrumentation fixed to the rotating testing platform disc 15 and for data transfer is eliminated. However, if, in certain applications, there is a need for sensory devices such as accelerometers to be mounted on the testing platform disc 15, then the rotary shock loading machine 10, FIGS. 1 and 2, may be provided with slip rings 39, which can be attached as shown in FIGS. 1 and 2, with one ring fixed to the shaft 18 and the other ring fixed to the bearing 19, thereby being kept fixed to the machine structure. In the embodiment, the shaft 18 is made out of a hollow tubing and the wiring for power and data transfer is then be passed from the slip ring component that is attached to the shaft 18 through a hole into the hollow shaft and out of the front and/or back surfaces of the testing platform disc 15 for attachment to the provided instrumentations.

It will be appreciated by those skilled in the art that during firing in a rifled barrel, munitions are subjected to a high acceleration pulse (shock loading). In the rotary shock loading and similar to commonly used shock loading machines used to simulate firing setback acceleration for testing various munitions components and systems, the component being tested is subjected to a similar deceleration pulse profile, which would have similar effects on the dynamic and structural behavior of the component 17 that is being tested.

Figure 4:
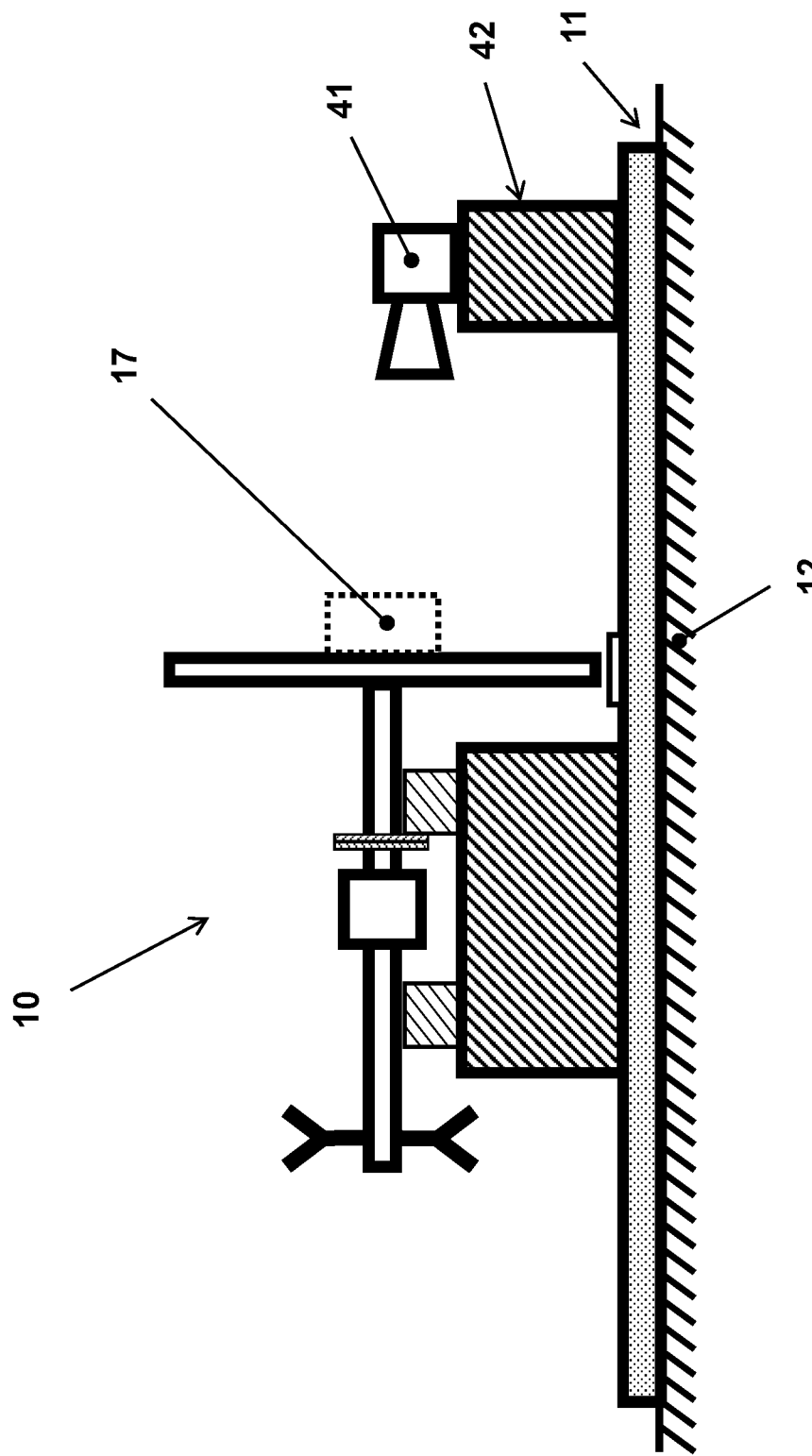
FIG. 4 illustrates the schematic of the mechanical rotary shock-testing machine of FIGS. 1 and 2 with a high-speed video camera to record the dynamic behavior of the components being tested.

In many cases, while subjecting the component being tested 17, FIGS. 1 and 2, to rotary shock loading, it is highly desirable to observe the dynamic behavior of the various components and structure of the device(s) being tested. For this purpose, a high speed camera 41 may be provided on a platform 42, which can be attached rigidly to the base plate 11, as shown in FIG. 4 to record the dynamic behavior of the moving parts, structure and other parts of the component being tested 17. To this end, the high-speed videoing may be synchronized with the rotary shock loading pulse by providing a simple switching element (not shown) on the sliding locking member 33 or the piston 38 of the cylinder 37, FIG. 3, to simultaneously initiate the rotary shock loading pulse and the video camera 41.

In the embodiment 10 of the mechanical rotary shock-testing machine, FIGS. 1 and 2, the testing platform disc 15 is used directly as a braking disc to generate the required rotary shock loading toque pulse. However, it might be desirable to have a separate braking disc so that the entire front and back surfaces of the testing platform disc 15 is available for mounting the testing components 17. The provision of a separate braking disc allows the use of smaller diameter testing platform disc 15, which is highly desirable, particularly for testing machines designed for operation at high spin rates. In addition, wear due to the braking action of the braking pads on the surfaces of the testing platform disc 15 is eliminated, thereby minimizing system maintenance requirement. This is particularly beneficial since separate braking discs will be significantly cheaper than testing platform disc 15 and the present mechanical rotary shock testing machine can be designed as described below, such that the braking disc can be readily replaced.

Figure 5:
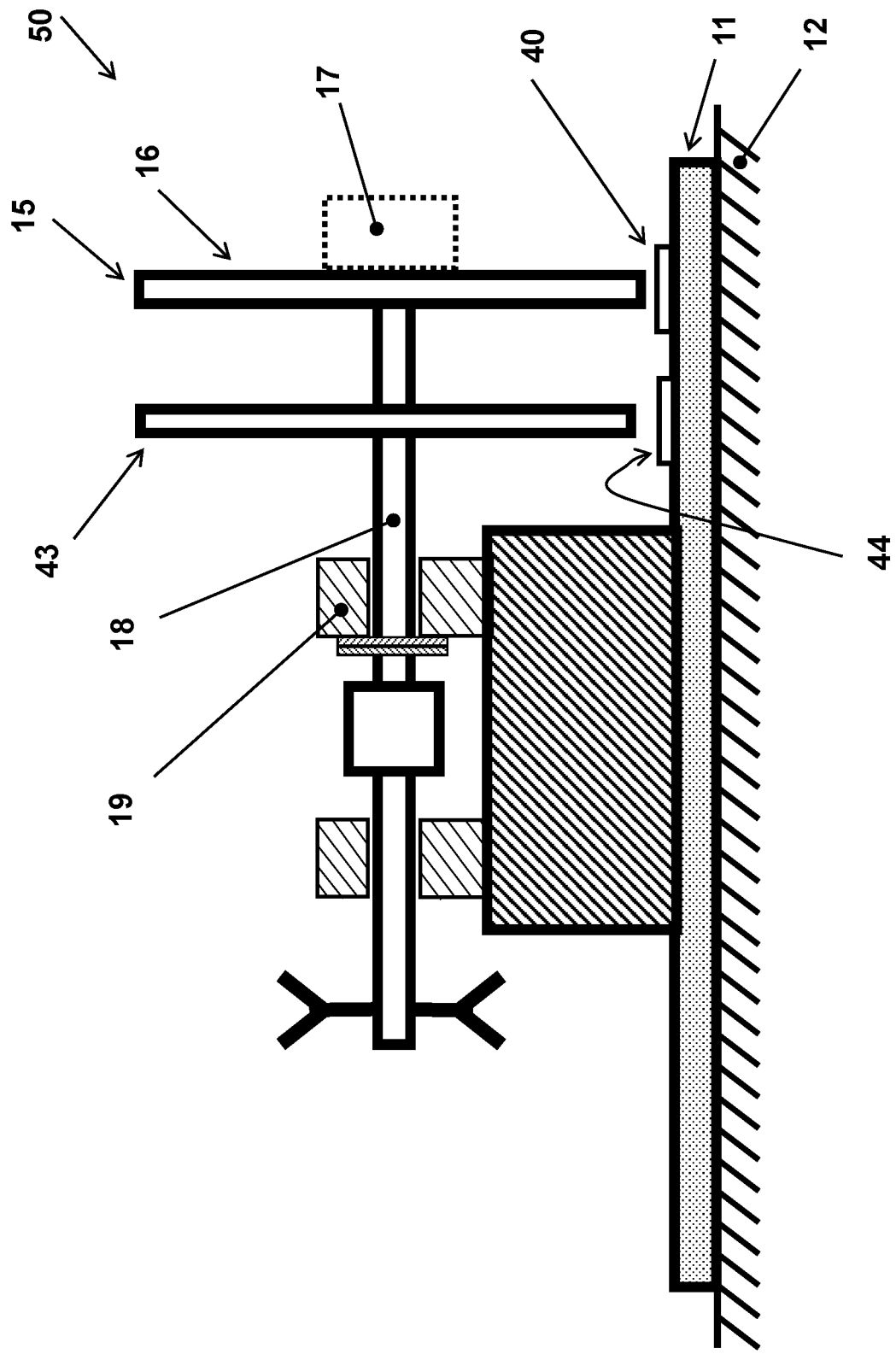
FIG. 5 illustrates the schematic of a cross-sectional side view of the second basic embodiment of the mechanical rotary shock-testing machine.

Such an embodiment 50 of the mechanical rotary shock testing machine of the present invention is shown in the schematic of FIG. 5. In the embodiment 50 of FIG. 5 all components of the mechanical rotary shock testing machine are identical to those of the embodiment 10 of FIGS. 1 and 2, except for the addition of at least one braking disc 43 as described below. In this embodiment 50, the rotary shock loading is applied to the component being tested 17 by the at least one braking unit 26, FIGS. 2 and 3, but the braking forces are applied to the provided at least one braking disc 43 instead of being applied directly to the testing platform disc 15. The at least one braking disc 43 is fixedly attached to the shaft 18, FIG. 5, which can be as close as possible to the testing platform disc 15 to minimize the torsional deflection of the section of the shaft 18 between the discs 43 and 15. The braking pads 27 of the at least one braking unit 26, FIG. 3, would similarly engage the surfaces of the braking discs 43 to apply the desired rotary shock loading deceleration pulse to testing platform disc 15, thereby to the component 17 which is being tested under rotary shock loading.

It will be appreciated by those skilled in the art that the sensor 40, FIG. 1, used for measuring the position, velocity and acceleration of the testing platform disc 15 may be positioned as indicated by the numeral 44 in FIG. 5 to make the same measurements with the aforementioned optical or the method using the braking disc 43.

The braking units 26 shown in the schematic of FIG. 3 are designed to apply braking force to one or the other surface of the testing platform disc 15 or independently to both sides of the said disc as shown in FIG. 2. The braking units 26 similarly applies braking forces to one or independently to both sides of the disc brakes 43 of the mechanical rotary shock testing machine embodiment 50 shown in the schematic FIG. 5. It will be, however, appreciated by those skilled in the art that the best method of applying braking forces to a rotating disc is by applying equal but opposite forces to the sides of the disc and with the resultant force being as collinear as possible so that they would not subject the disc to a bending moment. As a result, the braking disc can be relatively thin, thereby reducing the overall system moment of inertia and the decelerating friction generated torque needed to apply a prescribed deceleration rate to the components being tested 17. In addition, the braking force that has to be provided by the preloaded springs 31 or the hydraulic or pneumatic cylinder 37, FIG. 3, is significantly reduced, thereby reducing the required structural strength and therefore the inertia of the moving components of the braking units 26, making it possible for the braking pads to fully engage the braking disc significantly faster.

The basic method of applying equal but opposite braking forces to a rotating disc is well known in the art and are known as floating caliper or swinging caliper type brakes. Various types of such calipers have long been used on bicycle rim brakes. They are also widely used in many vehicle disc brakes. In such brakes, instead of the sliding member 29 of the braking units 26 shown in FIG. 3, which only allow the brake pad to move straight in and out towards the rotating disc (15 in FIGS. 2 and 43 in FIG. 5), a swinging caliper utilizes a single vertical pivot located somewhere away from the axis of rotation of the disc as observed in the top view of FIG. 2. This basic method of applying equal but opposite braking forces to rotating disc is shown in the schematic of FIG. 6.

Figure 6:
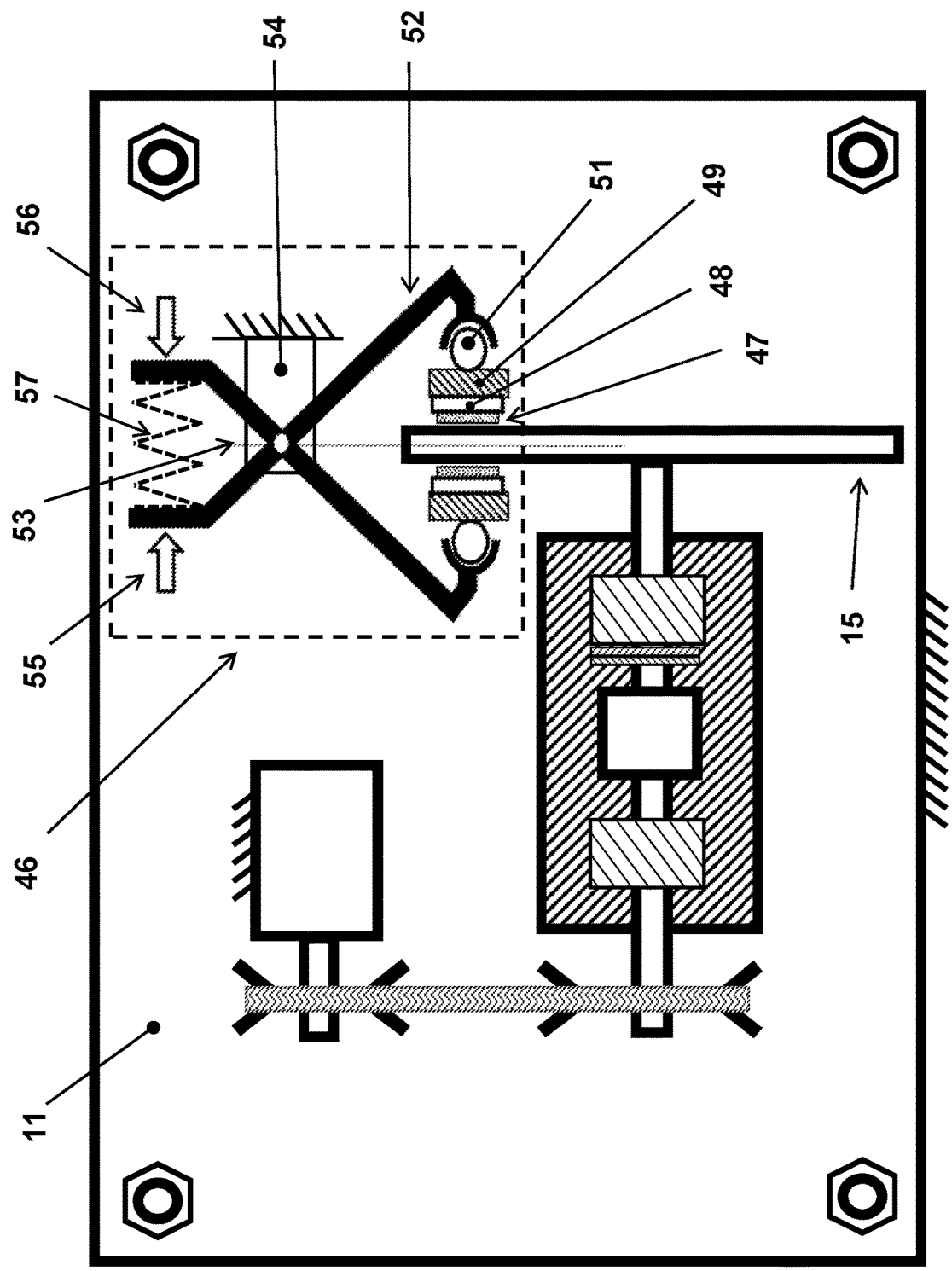
FIG. 6 illustrates the schematic of the mechanical rotary shock-testing machine of FIGS. 1 and 2 with an alternative braking unit for applying equal and opposite braking forces to the rotary disc.

In the schematic of FIG. 6, the basic design of a swinging caliper type braking unit 46, indicated by the dashed line rectangle, is shown as positioned for braking the testing platform disc 15 of the mechanical rotary shock testing machine embodiment 10 of FIGS. 1 and 2. It is however appreciated by those skilled in the art that such swinging caliper type braking units 46 may be similarly used to apply equal and opposite braking forces to the at least one disc brakes 43 of the embodiment 50 of FIG. 5.

A swinging caliper type braking unit such as the unit 46 shown in FIG. 6 consists of a pair of braking pads 47, which are mounted on backing plates 48. The backing plates 48 are in turn attached to relatively rigid pressure application plates 49. In general, even though the braking pad may be attached directly to the pressure application plates 49, they are instead attached (usually by a firm adhesive) to intermediate backing plates 48 for ease of replacement. The pressure application plates 49 are attached to scissor-type mechanism links 52 of the swinging caliper type braking unit 46 by spherical or rotary (pin) joints 51. The two links 52 of the scissor-type mechanism are connected together at the joint 53, the pin of which can be fixed to support structure 54, which is in turn fixedly attached to the base plate 11. Alternatively, a separate rotary joint may be provided under the rotary joint 53, with its pin being fixedly attached to the base plate 11 and serve as the aforementioned vertical pivot of the present swinging caliper type braking unit 46. Now, by applying equal but opposite forces to the end ("handle" of the scissor-type mechanism of the swinging caliper type braking unit 46) as indicated by the location and direction by the arrows 55 and 56 in FIG. 6, then the breaking pads 47 will apply an equal and opposite force to the testing platform disc 15 (or to the at least one disc brakes 43, FIG. 5, when used). As a result, no bending forces will be applied to the braking disc 15 (43), and the disc can be made relatively thin and therefore light.

The equal and opposite forces 55 and 56 may be applied, for example, by a provided compressively preloaded spring 57, which is released when it is desired to apply the brake to decelerate the rotating disc as previously described. The brake release element may, for example, be a simple relatively rigid member (not shown) that is positioned between the ends of the links 52 (above the compressively preloaded spring 57 as seen in FIG. 6), and is pulled out to apply the brake. An example of such a release mechanism is shown in FIG. 7.

Figure 7:
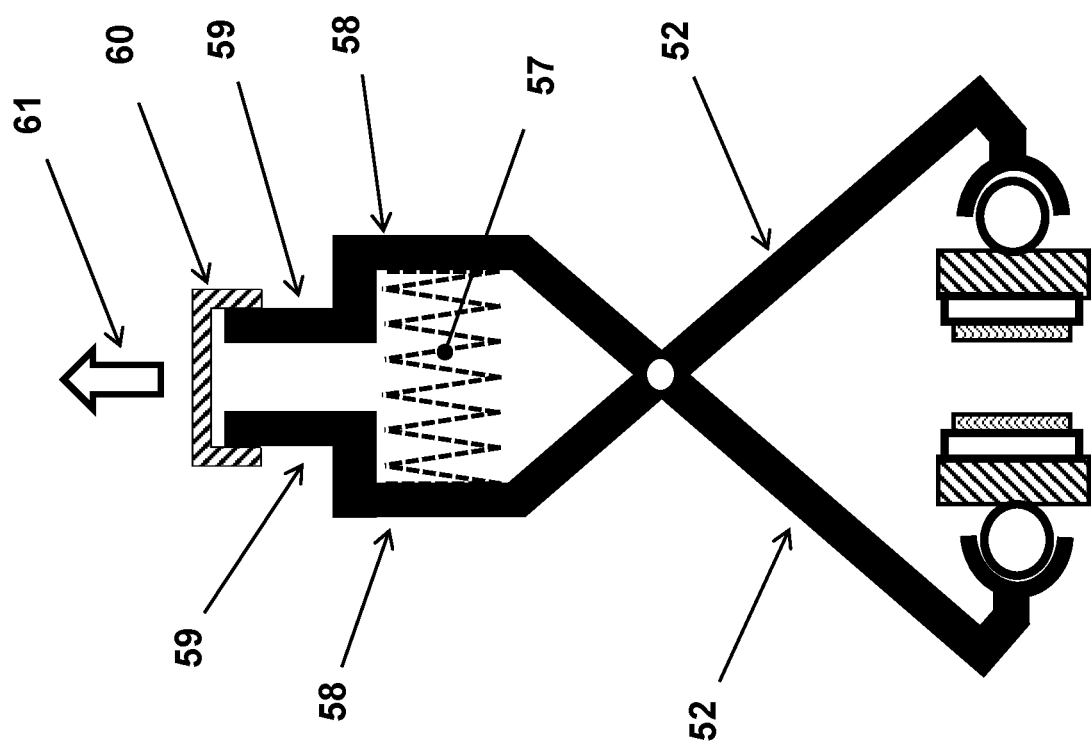
FIG. 7 illustrates the schematic of the braking units of the basic embodiment of the mechanical rotary shock-loading machine shown in the schematics of FIG. 6.

In the schematic of FIG. 7, the braking unit 46 of FIG. 6 is redrawn with a spring preload retaining and release mechanism. The spring preload retaining and release mechanism consists of the added structures 59, which can be integral to the links 52 of the scissor-type mechanism of the braking unit 46. A locking element 60 is then used to hold the links 52 in the desired preloading position of the compressive spring 57. Then, the operator can initiate braking force application by simply pulling the locking element in the direction of the arrow 61, thereby allowing the preloaded spring to apply the prescribed braking force to the rotating testing platform disc 15, FIG. 6, or the at least one disc brakes 43, FIG. 5. In this embodiment, the preloading force may be adjusted in several ways, depending on the amount of adjustment that is desired, including the provision (or removal) of spacers of appropriate thickness between the compressive spring 57 and the surface of one or both links 52. For relatively large compressive force adjustments, the number or size of Bellville washers and/or their stacking configuration may be varied. It will be appreciated by those skilled in the art that the primary objective in choosing the appropriate method is to achieve minimal gaps between the braking pads 47 and the braking discs, so that full braking force application can be achieved in minimal time.

Figure 8:
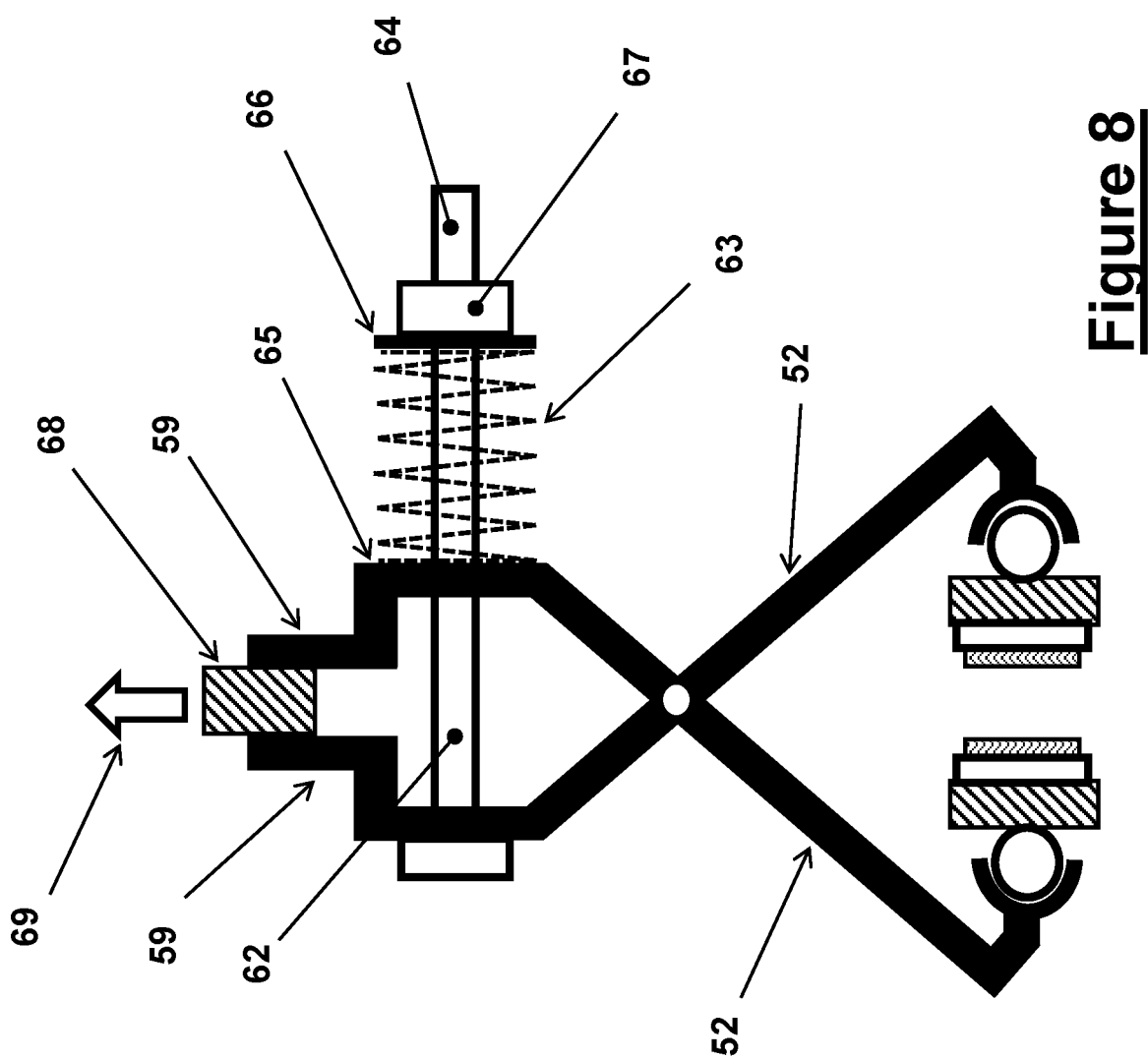
FIG. 8 illustrates the schematic of an alternative braking unit of the basic embodiment of the mechanical rotary shock-loading machine shown in the schematics FIG. 6.

An alternative preloaded compressive spring based braking unit mechanism is shown in the schematic of FIG. 8. This mechanism configuration is configured to make adjustment of the preloading force of the compressive spring easier to achieve and making its adjustment not to affect the spacing of the braking pads 47, FIG. 6, with the testing platform disc 15 or the at least one disc brakes 43, FIG. 5.

In the schematic of FIG. 8, the braking unit 46 of FIG. 6 is redrawn with the aforementioned spring preload retaining and release mechanism. Similar to the embodiment of FIG. 7, the spring preload retaining and release mechanism is provided with the structures 59, which can be integral to the links 52 of the scissor-type mechanism of the braking unit 46. A bolt 62 is passed through holes provided in the links 52 as shown in FIG. 8. The holes in the links 52 are slightly larger than the diameter of the passing bolt 62 so that it can freely move back and forth and rotate relative to the links. The preloading compressive spring 63 is then mounted over the threaded end 64 of the bolt 62 against the outer surface 65 of the link 52 as shown in FIG. 8. A load disturbing washer 66 can be provided over the preloading compressive spring 63 and the nut 67, which is used to apply the required preloading force level to the compressive spring 63 and adjust its level to the desired level. Before beginning the process of adjusting the preloading level of the compressive spring 63, a release member 68 is positioned between the inner surfaces of the structures 59 of the links 52. The width of the release member 68 is selected such that the braking pads 47, FIG. 6, clear the surfaces of the testing platform disc 15, FIG. 6, or the at least one disc brakes 43, FIG. 5. It will be appreciated that with this design configuration, the operator can readily adjust the preloading force level of the compressive spring 63 and when needed change the size, the number and stacking order of the Bellville washers that can be used in its construction. The used may obviously use any other type of compressive spring or a combination of various spring (elastic or even elastomeric) elements for this purpose. The operator can then initiate the braking force application by simply pulling the release member 68 in the direction of the arrow 69, thereby allowing the preloaded compressive spring 63 to apply the prescribed braking force to the rotating testing platform disc 15, FIG. 6, or the at least one disc brakes 43, FIG. 5.

For the sake of safety, it is appropriate that the locking element 60 in the embodiment of FIG. 7 and the release member 68 in the embodiment of FIG. 8 be pulled away in the direction of the indicated arrows to initiate the braking actions by long enough cables or other similar means to ensure safe operation of the machine in high rate rotary deceleration testing of various components, particularly those of munitions fired by rifled gun barrels.

It will be appreciated by those skilled in the art that in a manner similar to swinging caliper type braking mechanisms used in vehicles, one may use a hydraulic or pneumatic cylinder in place of the compressively preloaded spring 57 shown in FIG. 6 to apply the indicated equal and opposite forces 55 and 56 to brake the rotating testing platform disc 15, FIG. 6, or the at least one disc brakes 43, FIG. 5. One may even use a cable as used in bicycle caliper type rim brakes. Hydraulic pistons have the advantage of being capable of applying very large braking forces and are very easy to adjust the braking forces to the desired level and are the preferred method of braking force generation as long as they can apply the braking force fast enough to achieve the desired few millisecond application time experienced by gun-fired munitions in rifled barrels. The required pneumatic pistons will be significantly larger than hydraulic cylinders and will be significantly slower than hydraulic cylinders in applying the braking forces. However, if the required braking force levels and application times are acceptable, they are preferable to hydraulic cylinders due to their ease of use, force adjustment, maintenance and service as well as cost. The use of cables with bicycle caliper type rim brakes is possible, but only if the total moment of inertia of the rotating testing platform disc 15 and its other rotating components is relatively low since the amount of braking force that can be applied by such cables is relatively low and the brake activation time is relatively long.

In general, when very fast braking force application is desired, the method of braking can be based on using preloaded springs, such as preloaded compressive springs as shown in the schematic of FIG. 7. This method is preferred since compressively preloaded springs constructed by proper stacking of Bellville washers or the like can generate the required very high braking forces very rapidly by releasing the links of the braking unit scissor-type mechanism, for example, by the pulling of a locking element 60 as previously described. Bellville washers are relatively light, exhibit very high spring rate (constant), thereby require very short deformation to provide a very high preloading and total force application upon release. As a result, the braking unit can react very rapidly to the release of its preloading mechanism.

The level of required friction forces that the braking pads 27 and 47, FIGS. 3 and 6, respectively, must apply to the surfaces of the rotating testing platform disc 15, FIG. 6, or the at least one disc brakes 43, FIG. 5, to generate the required decelerating toque is dependent on the coefficient of friction between the braking pads and the contacting surfaces of the discs, and the effective disc radius $R_e$ as shown in FIG. 2, at which the resultant friction force is applied. If the magnitude of the effective equal and opposite forces applied by the above braking pads is $F_e$ and the coefficient of friction between the said braking pads and the surfaces of the said discs is μ, then the decelerating (braking) torque τ applied to the rotating testing platform disc 15, FIG. 6, or the at least one disc brakes 43, FIG. 5, is given by $$\tau = 2\mu F_e R_e \qquad (1)$$

The factor 2 in equation (1) is included to account for the fact that each of the two braking pads is applying the same effective force $F_e$. Now if for the embodiment of FIGS. 1 and 2 the combined moment of inertia about the axis of rotation of the testing platform disc 15, the payload 17, the shaft 18 and the inertia contributed by the coupling 25 and other components rotating with the said disc is given as $I_e$, then by the application of the torque τ, equation (1), the testing platform disc 15 is decelerated at a rate $\alpha_d$ given by $$\alpha_d = \frac{\tau}{I_e} \qquad (2)$$

If the initial rotary speed of the testing platform disc 15 is ω, then with the applied deceleration rate of $\alpha_d$, equation (2), the length of time t that will take for the testing platform disc 15 to be brought to a complete stop is $$t = \frac{\omega}{\alpha_d} \qquad (3)$$

The same relationships apply to all embodiments, such as the embodiment 50 of FIG. 5, assuming that proper effective radii $R_e$ and effective force $F_e$ are used.

In the spin acceleration shock testing machines described above and discussed with regard to FIGS. 1-8, the spin acceleration occurring during firing of spin stabilized rounds is simulated by the spin deceleration of a spinning test object. Also provided herein are spin acceleration shock loading machines in which the testing platform disc (15 in the embodiments of FIGS. 1, 2, 5 and 6) is accelerated from its stationary position to a prescribed spin rate at a preset acceleration rate. Such spin acceleration shock testing machines and the resulting basic apparatus embodiments are described below with regard to FIGS. 9-12.

Figure 9:
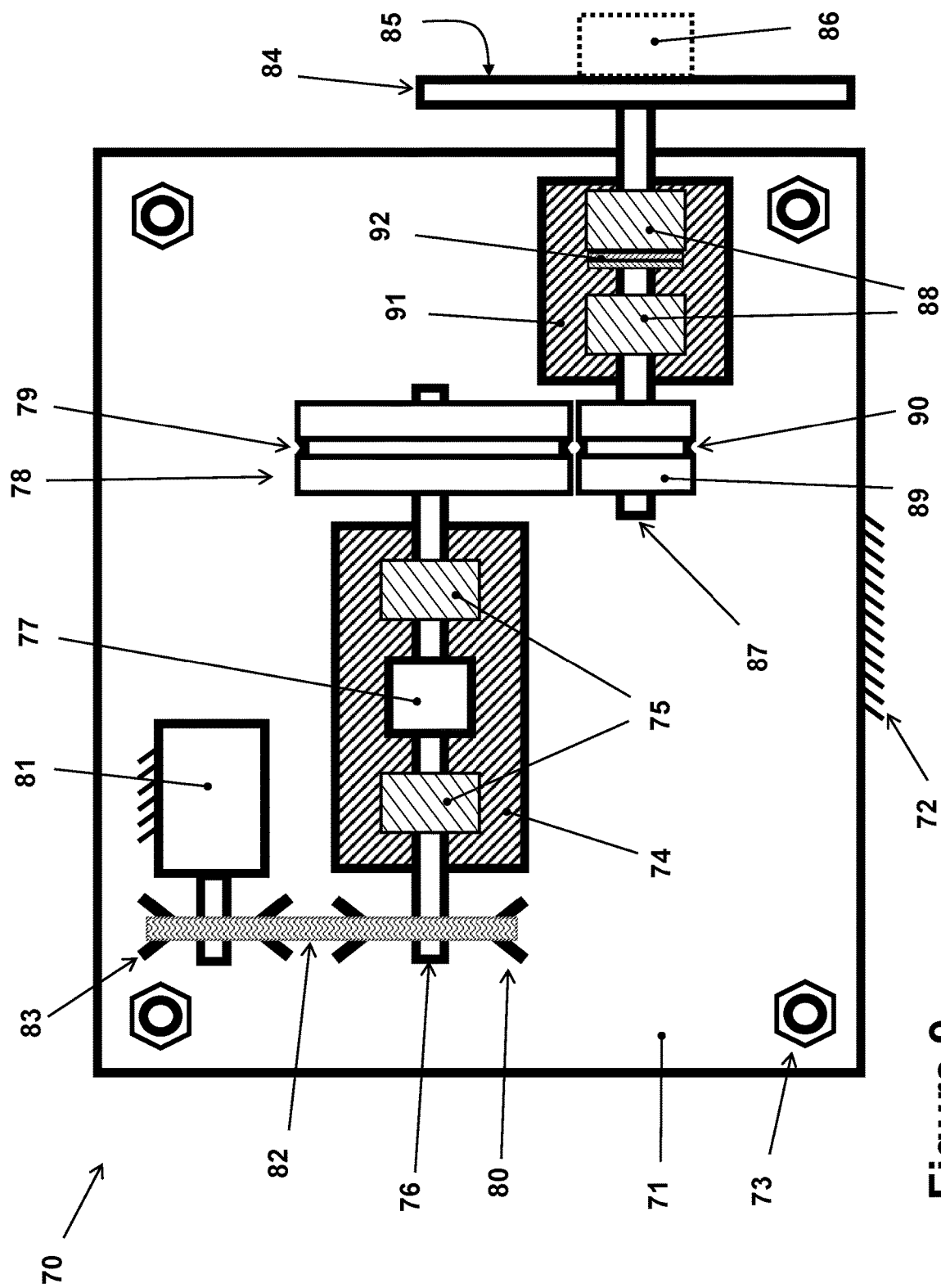
FIG. 9 illustrates an embodiment of a spin acceleration shock-loading machine in which the testing platform disc is accelerated from its stationary position to a prescribed spin rate at a preset acceleration rate.

Apparatus and methods for such spin acceleration shock loading machines in which the testing platform disc is accelerated from its stationary position to a prescribed spin rate at a preset acceleration rate is described with regard to a spin acceleration shock loading machine embodiment 70 of FIG. 9.

A top view of the mechanical rotary shock testing machine embodiment 70 is shown in FIG. 9. The mechanical rotary shock-testing machine 70 is constructed over a base plate 71, which can be made out of a heavy and thick steel plate, which is firmly anchored to the machine foundation 72 by at least four heavy anchoring bolts 73. The anchoring bolts 73 are positioned far enough apart around the base plate 71 to resist the high torque pulses (shocks) in reaction to the rotary shock loading pulses generated by the mechanical rotary shock testing machine 70. Certain relatively stiff shock absorbing elements (not shown) may be provided between the base 71 and the foundation 72 to prevent damage to the foundation structure. In heavier machinery, a relatively large (usually made out of reinforced concrete) foundation block (not shown) can be used with shock isolation elements having been positioned between the foundation block and the surrounding structure.

Similar to the embodiment 10 shown in the cross-sectional and top views of FIGS. 1 and 2, respectively, a rigid platform structure 74 is firmly attached to the base plate 71 and is used to rigidly attach the indicated rotary assembly of the mechanical rotary shock-testing machine to the base plate 71. The rotary assembly consists of bearing assemblies 75 which are attached to the platform structure 74, and which are used to rotatably support the shaft 76. The shaft 76 may be one piece or have two parts that are connected together by a coupling 77 as shown in FIG. 9, as was described for the shaft 18 for the embodiment of FIG. 1. In practice, multiple bearing units 75 can be used on each section of the shaft 76 to minimize its deflection and to allow it to be rotated at the highest operating speed that the machine is designed to operate.

A flywheel 78 is firmly attached to one end of the shaft 76 and a drive pulley 80 is attached to an opposite end of the shaft 76 as shown in FIG. 9. The flywheel 78 is provided with the central shallow groove 79 around its periphery. The shaft 76 and thereby the flywheel 78 is rotated by an electric motor 81 via a belt 82 and the motor pulley 83, FIG. 9. The electric motor 81 is firmly attached to the base plate 71. The speed of the electric motor 81 can be controlled by a controller, such as a computer (not shown) as is commonly done in various machinery.

The mechanical rotary shock testing machine 70 is also provided with a "testing platform disc" 84 (similar to the disc 15 in the embodiments of FIGS. 1-8), over the frontal surface 85 of which the components to be tested 86 are generally attached. The testing platform disc 84 is rigidly attached to a shaft 87, which is supported by bearings 88 mounted over a rigid platform structure 91, which is in turn fixedly attached to the base plate 71. In practice, multiple bearing units 88 can be used on each section of the shaft 87 to minimize its deflection and to allow it to be rotated at the highest operating speed that the machine is designed to operate.

The shaft 87 is also provided with a wheel 89, which is fixedly attached to the shaft 87. The wheel 89 is also provided with a peripheral groove 90 similar to the groove 79 on the periphery of the flywheel 78. The mechanical rotary shock testing machine embodiment 70 shown in FIG. 9 is assembled such that the shafts 87 and 76 are essentially parallel and such that the wheel 89 and the flywheel 78 are essentially lined up, with the grooves 90 and 79 on the wheel 89 and flywheel 78, respectively, facing each other. The wheel 89 and the flywheel 78 are also positioned very close to each other with a minimal clearance separating them. The clearance, depending on the desired shock loading test and the moment of inertial of the components (about the axis of rotation of the shaft 87) to be tested, can be of the order 1-4 millimeters, and can be adjustable. The clearance can be adjustable by the movement of the rigid platform structure 91.

During a spin acceleration test, the drive motor 81 is first used to bring the flywheel 78 to the desired spin rate to which the testing components 86 are desired to be accelerated to. At this point, the test platform disc 84 and thereby the testing components 86 are stationary. At this point, a strip of a relatively hard rubber or leather or the like high friction but relatively flexible material, which may have a sharpened or tapered tip (not shown) is suddenly fed between the flywheel 78 and the wheel 89, such as through the facing grooves 79 and 90. If the thickness and material properties of the high friction strip and the amount of clearance between the flywheel 78 and the wheel 89 are selected properly, then the strip will engage the flywheel 78 and the wheel 89, and quickly accelerate the wheel 89 to the rotary speed of the flywheel 78.

The wheels will then grab the strip and pull it between the two wheels while compressing it to fit their opening gap. By providing relatively rough surface on the flywheel and the friction disc, the flywheel would rapidly accelerate the friction wheel to its own speed. The rate of acceleration is dependent on the friction forces generated by the hard rubber or the like strip, which is dependent on the strip hardness, viscoelasticity and thickness, and the provided clearance between the flywheel 78 and the wheel 89.

It will be appreciated by those skilled in the art that depending on the amount of friction to be generated between the high friction strip and the surfaces of the flywheel 78 and the wheel 89, the high friction strip may be relatively small and fit between the grooves 79 and 90, or when larger friction forces, i.e., higher spin acceleration rates are desired, a wider band of such high friction strip may be used between the surfaces of the flywheel 78 and the wheel 89. In general, the surfaces of the flywheel 78 and the wheel 89 are desired to be relatively rough and non-slippery. The surfaces of the flywheel 78 and the wheel 89 may also be covered by high friction materials such as hard rubber to further increase friction and achieve higher spin acceleration rates. In general, when higher spin acceleration rates are desired, the grooves 79 and 90 may be eliminated to allow the introduction of wider high friction strips between the flywheel 78 and the wheel 89.

It will be appreciated by those skilled in the art that the sensor 40, as shown in FIG. 1, used for measuring the rotary position, velocity and acceleration of the testing platform disc 15 may also be positioned similarly, such as under the testing platform disc 84 of the mechanical rotary shock testing machine 70 of FIG. 9 to make the same measurements with the aforementioned optical or the like method. Alternatively, or as a second means of making the same measurement of the rotary position, velocity and acceleration of the testing platform disc 84, the mechanical rotary shock testing machine 70 of FIG. 9 may be provided with slip rings 92, which can be attached as shown in FIG. 9, with one ring fixed to the shaft 87 and the other ring fixed to the bearing 88, thereby being kept fixed to the machine structure.

In the spin acceleration shock testing machine described above and the resulting embodiments shown in the schematics of FIGS. 1-9, the spin acceleration occurring during firing of spin stabilized rounds is simulated by the spin deceleration of a spinning test object in the embodiments of FIGS. 1-8, and by providing spin acceleration shock loading to a stationary testing platform disc (84 in the embodiment of FIG. 9) to a prescribed spin rate at a preset acceleration rate. Methods for the design of such spin acceleration shock testing machines and the resulting basic apparatus embodiments were also described in detail.

However, since during firing of munitions in rifled barrels, the munitions is subjected to linear acceleration in the direction of its travel inside the barrel as well as the aforementioned spin acceleration about the direction of its travel, therefore, also provided are methods of designing and constructing shock loading machines that can impart a combination of linear acceleration shock loading as well as spin acceleration shock loading to the munitions systems and/or its components to be tested. It will be appreciated by those skilled in the art that in munitions firing in rifled barrels, the spin acceleration rate and the linear acceleration rates are related and are not independent with the relationship being dependent on the pitch of the rifling inside the barrel.

Figure 10:
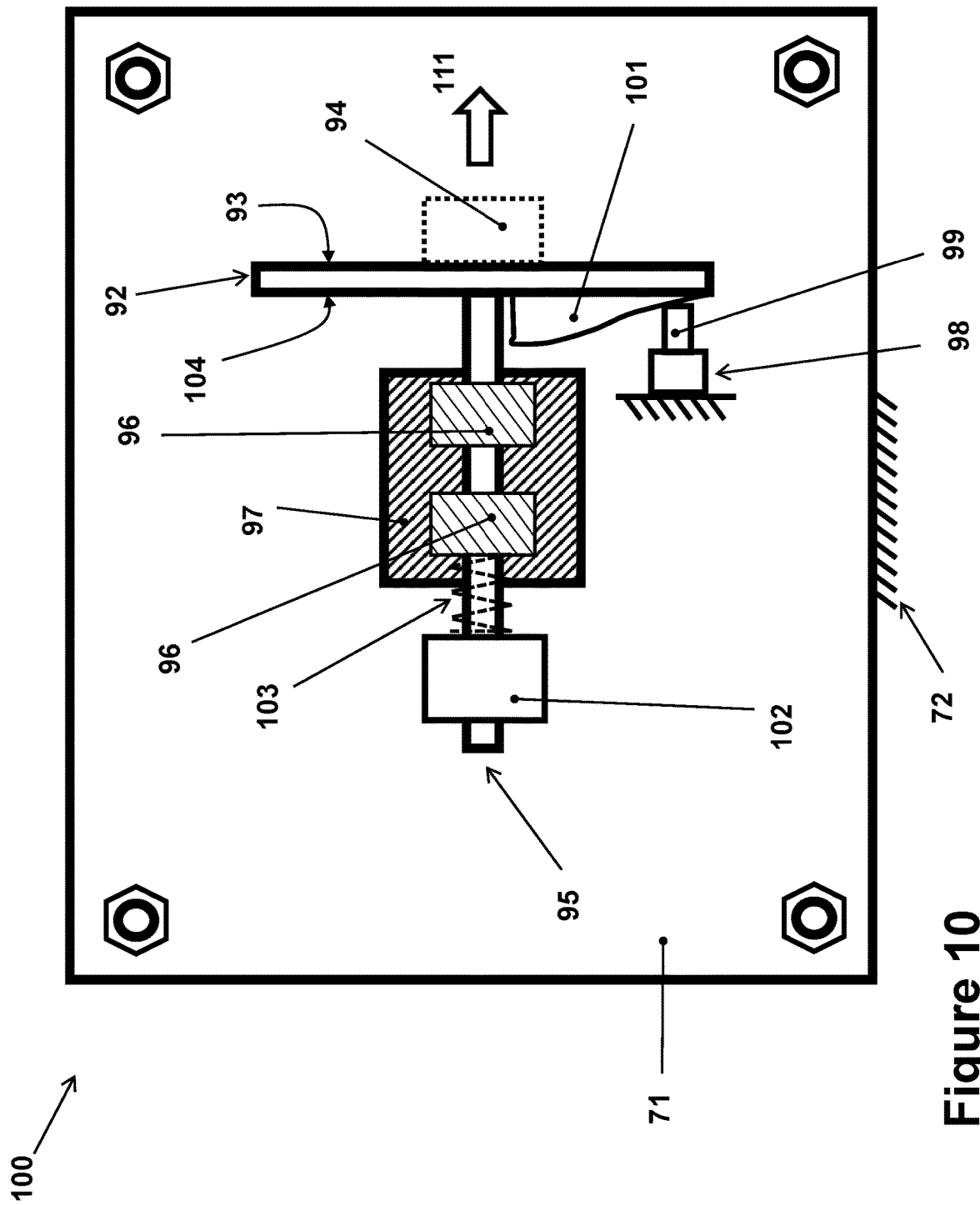
FIG. 10 illustrates an embodiment of a shock-loading machine that is used to apply a combined spin and linear acceleration shock similar to those experienced by munitions fired in rifled barrels.

Such shock testing machines that can subject test components and systems to a combination of high rotary and linear acceleration shock loading similar to those experienced during firing by rifled barrels and a typical resulting shock testing machine is described using the embodiment 100 of FIG. 10. All components of the embodiment 100 of FIG. 10 are identical to those of the embodiment 70 of FIG. 9, except for the testing platform disc 84 assembly, which is not shown in the schematic of FIG. 10.

In the mechanical shock testing machine 100, a similar "testing platform disc" 92 (84 in the embodiment of FIGS. 9 and 15 in the embodiments of FIGS. 1-8) is also provided, over the frontal surface 93 of which the components to be tested 94 are generally attached. The testing platform disc 92 is rigidly attached to the shaft 95, FIG. 10, which is supported by bearings 96, which are mounted over the rigid platform structure 97, which is in turn fixedly attached to the base plate 71. In practice, multiple bearing units 96 can be used on the shaft 95 to minimize its deflection and to allow it to be translated and rotated at the highest operating speed that the machine is designed to operate.

In the above embodiments, the testing platform disc shafts (87 in the embodiment of FIGS. 9 and 18 in the embodiments of FIGS. 1 and 5) are attached to the machine support structure (91 in the embodiment of FIGS. 9 and 14 in the embodiment of FIG. 1) by rotary bearings (88 in the embodiment of FIGS. 9 and 19 in the embodiment of FIG. 1), which allow the shafts to freely rotate but not translate relative to the bearings. However, in the embodiment 100 of FIG. 10, testing platform disc shaft 95 is attached to the rigid platform structure 97 by bearings 96, which allow the shaft 95 to freely rotate as well as translate along rotary axis of the shaft. A similar friction wheel 102 (89 in the embodiment of FIG. 9 but without the peripheral groove 90) is also provided and similarly fixedly attached to the shaft 95).

A relatively soft and lightly preloaded compressive spring 103 can be provided between the friction wheel 102 and the bearing 96 as shown in FIG. 10 to keep a cam follower 99 in continuous contact with the surface of the cam 101, which is provided on the back surface 104 of the testing platform disc 92, as is shown in the schematic of FIG. 10. The cam follower 99 is attached to the base plate 71 by the support 98. The cam 101 is provided at a radial distance on the indicated back surface 104 of the testing platform disc 92 so that as it is rotated during spin acceleration shock loading as was described for the embodiment of FIG. 9, testing platform disc 92 is simultaneously accelerated forward, thereby applying a combined spin acceleration and linear acceleration to the munitions system or components 94 that are tested. As a result, the munitions system or components 94 that are tested are subjected to a shock-loading event that is very similar to that experienced during firing by rifled munitions.

The view of the back surface 104 of the testing platform disc 92 of the mechanical shock testing machine embodiment 100 of FIG. 10 is shown in FIG. 11. The view of the testing platform disc 92 in the direction of the arrow 105 is shown in FIG. 12. As can be seen in the back surface 104 view of FIG. 11, the cam 106 (101 in the schematic of FIG. 10) is seen to be positioned at a fixed radial distance from the rotating shaft 95 of the testing platform disc 92. Initially, while the testing platform disc 92 is stationary, the cam follower 99 is positioned close to the start 107 of the (rising) cam surface 108. Then as the friction wheel 102 (FIG. 10) engages the flywheel 79 (FIG. 9) by the introduction of the aforementioned strip of a relatively hard rubber or leather or the like high friction but relatively flexible material which can have a sharpened or tapered tip (not shown) between the flywheel 79 and the friction wheel 102, the testing platform disc 92 is rotationally accelerated in the counterclockwise direction as seen in the view of FIG. 11. As a result, the cam follower 99 (FIGS. 10 and 12) begins to roll over the surface 108 (FIGS. 11 and 12) of the cam 106 (101 in the schematic of FIG. 10), thereby pushing (linearly accelerating) the testing platform disc 92 in the direction of the arrow 111 shown in FIG. 10, while the testing platform disc 92 is also being rotationally accelerated as was previously described for the embodiment 70 of FIG. 9. The testing platform disc 92 is accelerated in the direction of the arrow 111, FIG. 10, until the cam follower 99 reaches the flat surface 109 (FIGS. 11 and 12) of the cam 106, by which time the cam 106 would have translated the testing platform disc 92 a distance 110 shown in FIG. 12.

It will be appreciated by those skilled in the art that when the testing platform disc 92 is to be rotated in the clockwise direction further than the provided flat surface 109 (FIGS. 11 and 12) for the cam follower 107 to travel, then the flat surface 109 may be extended as needed as shown by the dashed lines in FIG. 11 and as indicated by the numeral 112.

It will also be appreciated by those skilled in the art that the slope of the surface 108 of the cam 106, FIGS. 11 and 12, relates the relationship between the spin acceleration of the testing platform 92 and its linear acceleration in the direction of the arrow 111, FIG. 10, i.e., higher the slope of the surface 108, higher linear acceleration would result for a given rotary (spin) acceleration of the testing platform 92 and thereby that of the munitions system or components being tested.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A rotary shock-testing machine comprising:
    a base;
    a first shaft rotatable relative to the base, the first shaft being driven to rotate;
    a first wheel rotatable with the first shaft;
    a second shaft rotatable relative to the base;
    a second wheel rotatable with a first portion of the second shaft; and
    a test disc for holding one or more specimens to be tested, the test disc being rotatable with a second portion of the second shaft;
    wherein the first and second wheels are aligned with each other such that the second wheel is driven by the first wheel when a material is introduced into a gap between a surface of the first wheel and a corresponding surface of the second wheel.

2. The rotary shock-testing machine of claim 1, further comprising one or more bearings for rotatably supporting each of the first and second shafts.

3. The rotary shock-testing machine of claim 2, wherein the one or more bearings comprises two or more bearings and each of the first and second shafts comprise two or more shaft portions corresponding to each of the two or more bearings, and further comprising a coupling for coupling each of adjacent two or more shaft portions together.

4. The rotary shock-testing machine of claim 1, further comprising a motor operatively connected to the first shaft for rotatably driving the first shaft.

5. The rotary shock-testing machine of claim 1, wherein the first wheel is a flywheel.

6. The rotary shock-testing machine of claim 1, wherein the second wheel is a friction wheel.

7. A method for rotary shock-testing one or more specimens, the method comprising:
    mounting the one or more specimens to be tested to a test disc;
    rotating a first wheel unengaged with the test disc; and
    inserting a material in a gap between a surface of the first wheel and a corresponding surface of a second wheel to engage the first wheel with the second wheel, the test disc being rotatable with the second wheel.

* * * * *